(12) United States Patent
Liu et al.

(10) Patent No.: US 7,592,151 B2
(45) Date of Patent: Sep. 22, 2009

(54) REDOX POLYMERS FOR USE IN ELECTROCHEMICAL-BASED SENSORS

(75) Inventors: Zuifang Liu, Inverness (GB); James Jain Rodgers, Lochardil (GB); Geoffrey Ulue, Inverness (GB)

(73) Assignee: Lifescan, Inc., Milpitas, CA (US)

( * ) Notice: Subject to any disclaimer, the term of this patent is extended or adjusted under 35 U.S.C. 154(b) by 130 days.

(21) Appl. No.: 11/875,681

(22) Filed: Oct. 19, 2007

(65) Prior Publication Data
US 2008/0035479 A1 Feb. 14, 2008

Related U.S. Application Data

(60) Division of application No. 11/429,518, filed on May 4, 2006, now Pat. No. 7,429,630, which is a continuation of application No. 10/900,511, filed on Jul. 28, 2004, now Pat. No. 7,109,271.

(51) Int. Cl.
*C08F 271/02* (2006.01)
*C12Q 1/54* (2006.01)

(52) U.S. Cl. .......... 435/14; 525/279; 525/283; 525/297; 525/298; 435/4; 435/817

(58) Field of Classification Search .......... 525/279, 525/283, 297, 298; 435/4, 14, 817
See application file for complete search history.

(56) References Cited

U.S. PATENT DOCUMENTS

| | | | |
|---|---|---|---|
| 3,728,286 A | 4/1973 | Welters et al. | |
| 4,224,125 A | 9/1980 | Nakamura et al. | |
| 5,089,112 A | 2/1992 | Skotheim et al. | |
| 5,262,035 A | 11/1993 | Gregg et al. | |
| 5,312,590 A * | 5/1994 | Gunasingham | 204/403.1 |
| 6,284,478 B1 | 9/2001 | Heller et al. | |
| 6,485,703 B1 | 11/2002 | Coté et al. | |
| 6,932,894 B2 * | 8/2005 | Mao et al. | 204/403.06 |
| 2003/0042137 A1 | 3/2003 | Mao et al. | |
| 2003/0175985 A1 | 9/2003 | Fukuoka et al. | |

OTHER PUBLICATIONS

Bu, Hai-Zhi, et al., "NAD(P)H sensors based on enzyme entrapment in ferrocene-containing polyacrylamide-based redox gels", Analytical Chemistry, vol. 70, No. 20, pp. 4320-4325, 1998.
Hale, Paul D., et al., "Amperometric Glucose Biosensors Based on Redox Polymer-Mediated Electron Transfer", Analytical Chemistry, vol. 63, pp. 677-682, 1991.
Heller, Adam, Electrical Wiring of Redox Enzymes, Acc. Chem. Res. vol. 23, No. 5 1990, pp. 128-134.
Kuramoto, Noriyuki, et al., Property of thermo-sensitive and redox-active poly(N-cyclopropylacrylamide-co-vinylferrocene) and poly(N-isopropylacrylamide-co-vinylferrocene), Polymer, vol. 39 No. 3, pp. 669-675, 1998.
Saito, Takahiro, et al., "Characterization of poly(vinylferrocene-*co*-2-hydroxyethyl methacrylate) for use as electron mediator in enzymatic glucose sensor", Reactive & Functional Polymers 37 (1998) pp. 263-269.

* cited by examiner

*Primary Examiner*—Helen L. Pezzuto

(57) ABSTRACT

A redox polymer for use in an electrochemical-based sensor includes a hydrophobic polymer backbone (e.g., a hydrophobic poly(methyl methacrylate) polymer backbone) and at least one hydrophilic polymer arm (such as a hydrophilic oligo(N-vinylpyrrolidinone) polymer arm) attached to the hydrophobic polymer backbone. The redox polymer also includes a plurality of redox mediators (e.g., ferrocene-based redox mediators) attached to the at least one hydrophilic polymer arm.

2 Claims, 6 Drawing Sheets

REDOX POLYMERS FOR USE IN ELECTROCHEMICAL-BASED SENSORS

This is a divisional of U.S. application Ser. No. 11/429,518 filed May 4, 2006, now U.S. Pat. No. 7,429,630 B2, which is a continuation of U.S. application Ser. No. 10/900,511 filed Jul. 28, 2004, now U.S. Pat. No. 7,109,271 B2, which is incorporated herein by reference.

BACKGROUND OF INVENTION

1. Field of the Invention

The present invention relates, in general, to polymers and, in particular, to polymers for use in electrochemical-based sensors.

2. Description of the Related Art

The use of electrochemical-based sensors that employ a redox mediator and a redox enzyme in conjunction with an electrode(s) for the determination of an analyte in a liquid sample has become of heightened interest in recent years. Such electrochemical-based sensors are believed to be particularly suitable for continuous or semi-continuous monitoring of analytes (such as glucose) in bodily fluid samples (e.g., blood or interstitial fluid samples). For example, electrochemical-based glucose sensors employing a redox mediator, a redox enzyme and a working electrode can determine (i.e., measure) glucose concentration using relatively low potentials (e.g., less than 0.4 V vs SCE), thereby limiting any interfering responses at the working electrode. For a further description of electrochemical-based sensors, see, for example, U.S. Pat. Nos. 5,089,112 and 6,284,478, each of which is hereby fully incorporated by reference.

In electrochemical-based sensors, the redox mediator facilitates electron transfer between the redox enzyme(s) and an electrode(s) of the electrochemical-based sensor. For electrochemical-based sensors that require long term stability, such as continuous or semi-continuous electrochemical-based glucose sensors, it is essential that the redox mediator does not leach away from the vicinity of the electrode. Therefore, it is not desirable to employ readily leachable redox mediators (such as readily leachable ferricyanide, benzoquinone and low molecular weight, quinone derivatives, ferrocene, low molecular weight ferrocene derivatives, ruthenium complexes and osmium complexes) in electrochemical-based sensors. In addition, if the redox mediator is a substance that is harmful to humans or other subjects, leaching of the redox mediator into a human's or other subject's body is undesirable and thus should be avoided.

To prevent redox mediator leaching, chemical compositions wherein redox mediators are chemically attached to redox enzymes have been proposed for use in electrochemical-based sensors. The redox enzymes of such chemical compositions can, however, suffer from a deleterious decrease in enzyme activity.

Alternatively, redox mediators have also been attached to water-insoluble synthetic polymer chains, such as polysilozanes, in order to prevent leaching. Such chemical compositions, however, suffer from low flexibility, and thus a reduced mediation activity, due to their hydrophobic nature. Redox mediators have also been attached to siloxane polymer backbones using hydrophilic eythelene oxide spacer compounds. Nonetheless, since each hydrophilic ethyelene oxide spacer compound attaches only one redox mediator to the siloxane polymer backbone, the mediation capability of the chemical composition is unfavorably limited. Furthermore, redox mediators covalently attached directly to hydrophilic polymer backbones are not suitable for efficient and secure attachment to electrodes of an electrochemical-based sensor.

Still needed in the field, therefore, is a chemical composition that can prevent the leaching of redox mediators from the vicinity of an electrochemical-based sensor's electrode while maintaining the redox mediator's activity. In addition, the chemical composition should provide for an efficient and secure attachment to an electrode of an electrochemical-based sensor. Also needed is an electrochemical-based sensor employing such a chemical composition.

SUMMARY OF INVENTION

Redox polymers for use in electrochemical-based sensors according to embodiments of the present invention prevent the leaching of redox mediators from the vicinity of an electrochemical-based sensor's electrode while maintaining adequate redox mediator activity. In addition, the redox polymers can be efficiently and securely attached to an electrode of an electrochemical-based sensor.

Electrochemical-based sensors according to embodiments of the present invention include an electrode coated with a redox polymer that prevents a redox mediator included in the redox polymer from leaching away from the vicinity of the electrode while maintaining adequate redox mediator activity.

A redox polymer for use in an electrochemical-based sensor according to an embodiment of the present invention includes a hydrophobic polymer backbone (e.g., a hydrophobic poly(methyl methacrylate) polymer backbone) and at least one hydrophilic polymer arm (such as a hydrophilic oligo(N-vinylpyrrolidinone) polymer arm) attached to the hydrophobic polymer backbone. The redox polymer also includes a plurality of redox mediators (e.g., a plurality of ferrocene-based redox mediators) attached to each of the hydrophilic polymer arms.

The hydrophobic polymer backbone of redox polymers according to the present invention provides for the redox polymers to be efficiently and securely attached to the surface of an electrochemical-based sensor's electrode. Since the redox polymer includes a plurality of redox mediators, these redox mediators can be immobilized in the vicinity of the electrode. Such immobilization can provide long term stability to an electrochemical-based sensor that employs the electrode. In addition, since the redox mediators are attached to a polymer with hydrophilic polymer arm(s) and a hydrophobic backbone, electron transfer from an enzyme (a hydrophilic entity) to the electrode (a hydrophobic entity) is facilitated. Furthermore, enzyme-mediator interaction is aided by the highly accessible nature of redox mediators attached to the hydrophilic polymer arms of the redox polymer.

Also, an electrochemical-based sensor according to an embodiment of the present invention includes an electrode (such as a carbon electrode) and a chemical composition that includes a redox polymer coated on a surface of the electrode. The redox polymer of such an electrochemical-based sensor includes a hydrophobic polymer backbone, at least one hydrophilic polymer arm attached to the hydrophobic polymer backbone and a plurality of redox mediators attached to each of the hydrophilic polymer arms.

BRIEF DESCRIPTION OF DRAWINGS

A better understanding of the features and advantages of the present invention will be obtained by reference to the following detailed description that sets forth illustrative embodiments, in which principles of the invention are utilized, and the accompanying drawings in which like numerals represent like elements, of which.

DETAILED DESCRIPTION OF THE INVENTION

To be consistent throughout the present specification and for clear understanding of the present invention, the following definitions are hereby provided for terms used therein:

The term "redox mediator" refers to any chemical moiety capable of undergoing a reduction (accepting of an electron(s)) or oxidation (donation of an electron(s)) with both an electrode surface and an enzyme.

The term "hydrophilic" refers to any chemical species or subgroup with a high affinity for aqueous solutions, such as water. Therefore, a hydrophilic compound tends to be attracted to, dissolve in, or be absorbed in an aqueous solution.

The term "hydrophobic" refers to any chemical species or subgroup with a low affinity for aqueous solutions, including water. Therefore, a hydrophobic compound tends to repel and not be absorbed in an aqueous solution.

The term "redox polymer" refers to a polymer that has been modified (e.g., derivatized) to include a plurality of redox mediators.

Figure 1:
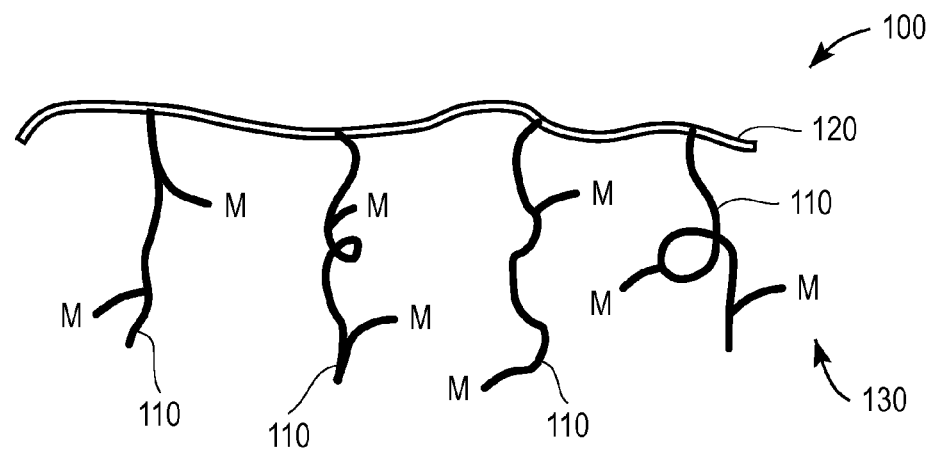
FIG. 1 is a simplified schematic depiction of a redox polymer for use in an electrochemical-based sensor according to an exemplary embodiment of the present invention.

FIG. 1 is a schematic depiction of a redox polymer 100 according to an exemplary embodiment of the present invention. Redox polymer 100 includes, a plurality of hydrophilic polymer arms 110 attached in a pendant manner (i.e., attached at a single point) to hydrophobic polymer backbone 120 of redox polymer 100. Each hydrophilic polymer arm 110 includes a plurality of redox mediators 130, schematically depicted by the letter "M" in FIG. 1. Such redox mediators can, for example, be covalently or otherwise attached to hydrophilic polymer arms 110.

Since hydrophobic polymer backbone 120 can be readily and securely attached to an electrode or other component of an electrochemical-based sensor (as described below), redox polymer 100 has the ability to immobilize redox mediator 130 in the vicinity of an electrochemical-based sensor's electrode. For example, hydrophobic polymer backbone 120 can be adhered to the surface of a carbon electrode via a hydrophobic interaction between hydrophobic backbone 120 and such a carbon electrode surface.

Furthermore, a plurality of redox mediators are attached to each hydrophilic polymer arm, the mediating capability of the redox polymer is not unduly limited. Moreover, although attached to a hydrophilic polymer arm, the redox mediators retain an adequate ability to favorably interact with a redox enzyme to exchange electrons and also to exchange electrons with an electrochemical-based sensor's electrode.

Hydrophobic polymer backbone 120 can be any suitable hydrophobic polymer backbone known to those of skill in the art, including a methylmethacrylate (MMA) based hydrophobic polymer backbone (e.g., a poly(methyl methacrylate) polymer backbone)). In this circumstance, the hydrophobic nature of MMA imparts a relatively high degree of hydrophobicity to the hydrophobic polymer backbone. Alternative hydrophobic monomers suitable for use in hydrophobic polymer backbones of redox polymers according to the present invention include, but are not limited to, hydrophobic acrylate monomers and hydrophobic vinyl monomers. Examples of such hydrophobic monomers are styrene monomers and butyl methacrylate monomers.

Figure 2:
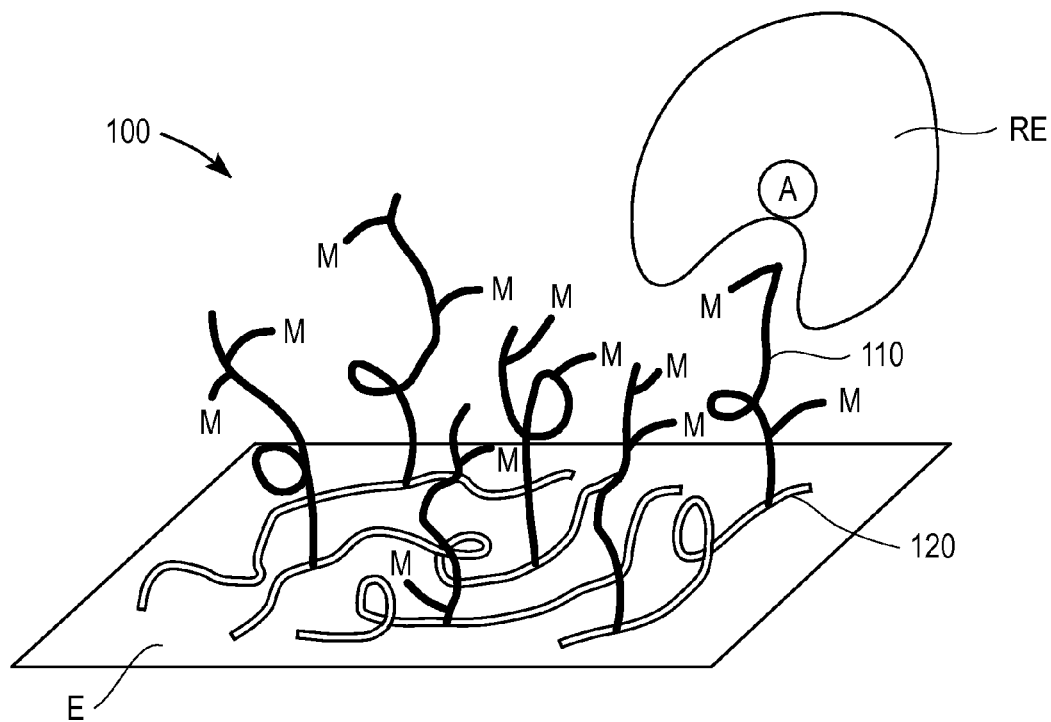
FIG. 2 is a simplified schematic representation of redox polymers according to exemplary embodiments of the present invention immobilized on an electrode of an electrochemical-based sensor.

Hydrophilic polymer arm 110 and attached redox mediators 130 can be any suitable hydrophilic polymer arm and redox mediator(s) combination known to those of skill in the art, including, for example, hydrophilic polymer arms with attached redox mediators formed from a combination of N-vinylpyrrolidinone (NVP) and vinyl ferrocene (VFc). Furthermore, the redox mediators of redox polymers according to the present invention can be any suitable redox mediator including, for example, ferrocene, osmium redox mediator complexes, quinone redox mediators, ferricyanide redox mediator, methylene blue redox mediator, 2,6-dichloroindophenol redox mediator, thionine redox mediator, gallocyanine redox mediator, indophenol redox mediator, and any combinations thereof FIG. 2 is a simplified schematic representation of four redox polymers 100 according to embodiments of the present invention immobilized on an electrode surface (E) of an electrochemical-based sensor. In the depiction of FIG. 2, one of the redox polymers 100 is shown interacting with a redox enzyme (RE) that includes an active site (A). FIG. 2 is a simplified depiction intended to illustrate the manner in which redox mediators M are capable of exchanging electrons with electrode surface E and redox enzyme RE.

One skilled in the art will recognize that redox enzyme RE is essentially a protein structure with an active site(s) A therein. Furthermore, active site A is a portion of redox enzyme RE that can selectively recognize an analyte (e.g., glucose) and exchange (i.e., donate or accept) an electron with the analyte.

In the depiction of FIG. 2, hydrophobic polymer backbones 120 are adsorbed, or otherwise adhered, to electrode surface E. This adherence results in redox polymer 100 being immobilized to electrode surface E such that redox polymer 100 (and redox mediators M) does not detach from and/or leach away from electrode surface E when the electrode surface is immersed in a liquid sample. Such adherence is a highly desirable attribute in electrochemical-based sensors, especially electrochemical-based sensors that measure glucose continuously in vivo and ex vivo, since redox mediator M can be toxic to humans. If redox mediator M were to leach away from the electrode surface, there is a risk that redox mediator M could enter a human body. In addition, since electrochemical-based sensors require redox mediator M for operation, it is important that the redox mediator not be capable of leaching from the vicinity of the electrode surface.

As depicted in FIG. 2, hydrophilic polymer arm 110 can be adapted to associate with redox enzyme RE such that pendant redox mediators M (i.e., mediators that are attached to the hydrophilic polymer arms at a single point) penetrate redox enzyme RE and become sufficiently close to active site A to enable electron transfer between redox mediator M and redox enzyme RE. Since there is a plurality of redox mediators M pendantly attached to each hydrophilic polymer arm 110, redox polymer 100 has a relatively high mediation conductivity. Such a relatively high mediation conductivity allows electrons to transfer from one redox mediator entity to another redox mediator entity. In addition, as hydrophilic arm 110 is highly flexible, it is able to diffuse between redox enzyme RE and electrode surface E, thereby transferring electrons from active site A to electrode surface E. In this regard, the term "flexible" refers to the relative freedom of the hydrophilic arms to move within a volume. This flexibility is a factor of the length of the hydrophilic arms, their crosslink density, and the inherent thermal and crystalline or amorphous characteristics of the polymer material from which the hydrophilic arms are formed.

Redox polymers can be formed by any suitable technique known to those of skill in the art. For example, FIG. 3 is a simplified depiction of a reaction sequence for synthesizing a redox polymer 300 according to an exemplary embodiment of the present invention.

The reaction sequence of FIG. 3 includes co-polymerizing NVP and VFc to form Compound 1 (see step 1 of FIG. 3), derivatizing Compound 1 to form Compound 2 (see step 2 of FIG. 3), and subsequently grafting Compound 2 to MMA (see step 3 of FIG. 3) to form redox polymer 300. One skilled in the art will recognize that redox polymer 300 can be characterized as an amphiphilic graft copolymer bearing covalently attached redox mediator moieties (namely, ferrocence moieties). As will be described in the Examples below, such a redox polymer is useful in electrochemically-based glucose sensors.

Figure 3:
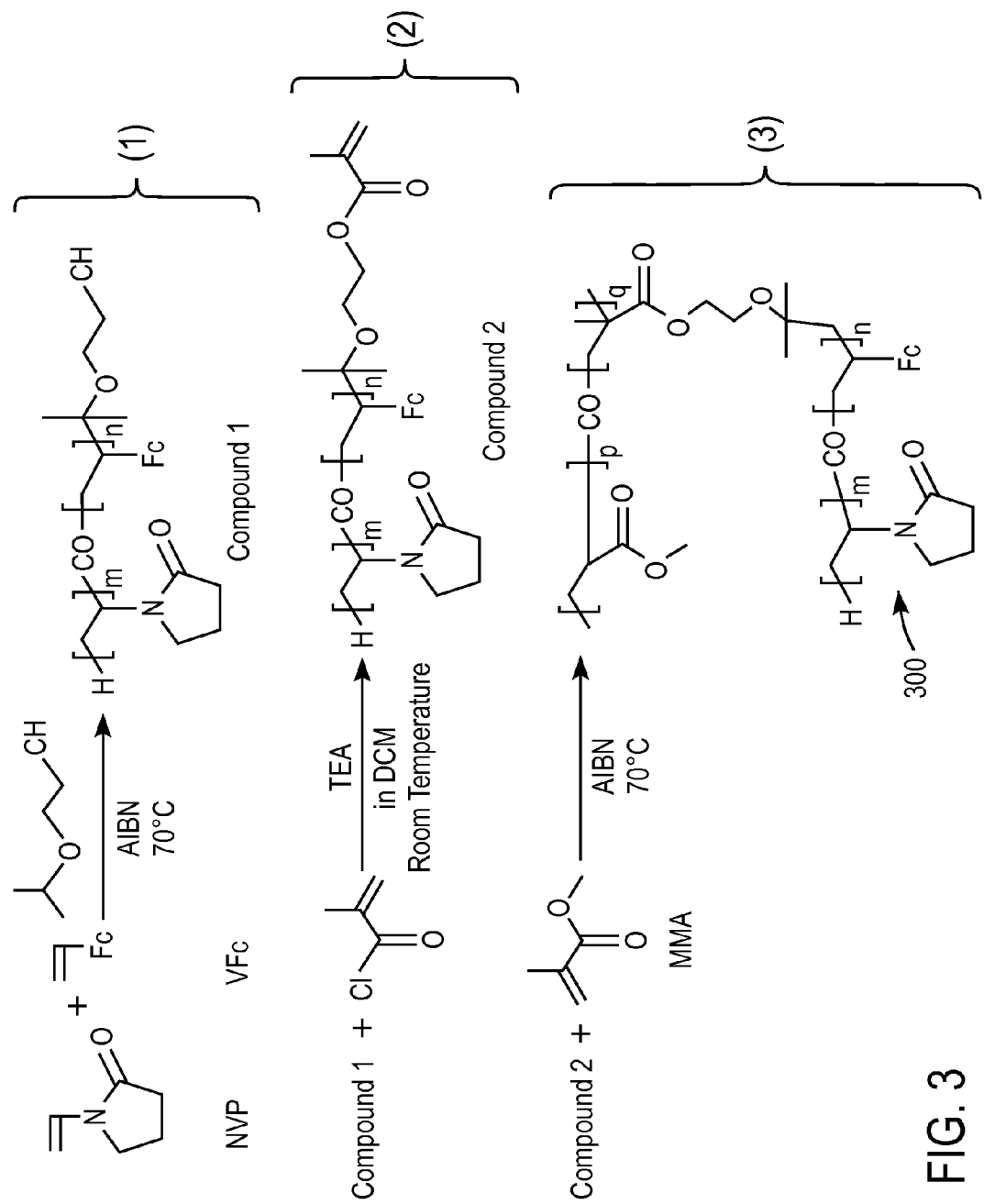
FIG. 3 is a simplified depiction of a reaction sequence for synthesizing a redox polymer according to an exemplary embodiment of the present invention.

In FIG. 3, the mole ratio of NVP to VFc in each of the hydrophilic polymer arms of redox polymer 300 is represented as m:n. Furthermore, the mole ratio of MMA monomers in the hydrophobic polymer backbone of redox polymer 300 to hydrophilic polymer arms of redox polymer 300 is represented as p:q. In addition, one skilled in the art will recognize that the redox mediator of redox polymer 300 is ferrocene (Fc).

The co-polymerization of step 1 in FIG. 3 can be performed in the presence of isopropoxyethanol (IPEtOH) to assist in quenching the co-polymerization and functionalizing the ends of Compound 1 with a hydroxyl group. In the reaction sequence of FIG. 3, Compound 1 can be referred to as oligo (N-vinylpyrrolidone) with ferrocene moieties and has, for example, a molecular weight in the range of from about 5,000 to 15,000 grams/mole. Furthermore, the mole ratio of NVP: VFc (i.e., m:n) of Compound 1 can, for example, be in the range of about 100:1 to about 100:5. In addition, the mole ratio of IPEtOH:NVP employed in step 1 of FIG. 3 can be, for example, in range from about 0.5:1 to about 3:1. Once apprised of the present invention, one skilled in the art will recognize that Compound 1 will form a hydrophilic polymer arm with a plurality of redox mediators in redox polymer 300. One skilled in the art will also recognize that conventional polymerization techniques will create hydrophilic polymer arms with a statistical distribution of redox mediators attached thereto. However, the polymerization techniques can readily be conducted such that a significant proportion of such hydrophilic polymer arms include a plurality of redox mediators and the hydrophilic polymer arms can, on average, include a plurality of redox mediators.

In the reaction sequence of FIG. 3, the ratio of IPEtOH to NVP predetermines the molecular weight of Compound 1. A relatively high proportion of IPEtOH will result in Compound 1 being of relatively low molecular weight. Conversely, a relatively low proportion of IPEtOH will result in Compound 1 being of relatively high molecular weight. The molecular weight of Compound 1 can, therefore, be predetermined such that the hydrophilic polymer arms of redox polymer 300 are long enough and flexible enough to enable rapid electron exchange between mediators attached to the hydrophilic arms and a redox enzyme. However, it has been determined that if the hydrophilic arms of redox polymer 300 are too long, redox polymer 100 can detach from an electrode surface. In accordance with the molecular weight range noted above and mole ratio of m:n, the average number of VFc's per Compound 1 can be, for example, in the range of from greater than 1 to about 7.

It should be noted that it is the hydrophilic character of NVP that imparts the relatively high degree of hydrophilicity to the hydrophilic polymer arms of redox polymer 300. Alternative hydrophilic monomers having acrylate or vinyl polymerizable functional groups can also be used in redox polymers according to exemplary embodiments of the present invention such as, for example, hydroxyethyl methacrylate, N-isopropylacrylamide, glycerol methacrylate and acrylamide. One skilled in the art will recognize that to employ different redox mediators and/or different hydrophilic monomers, changes should be accordingly made to the synthetic sequence of FIG. 3.

At step 2 of FIG. 3, Compound 1 is derivatized with methacroylchloride to form a methacrylate end functionalized macromonomer (Compound 2). Compound 2 has an acrylate group capable of forming a graft copolymer with the hydrophobic polymer backbone of redox polymer 300.

At step 3 of FIG. 3, Compound 2 is copolymerized with MMA to form redox polymer 300. It should be noted that following step 3, Compound 2 has essentially been transformed into the hydrophilic arms of redox polymer 300. Redox polymer 300 is an amphiphilic graft co-polymer with the characteristic of adhering strongly to an electrode and the ability to exchange electrons with redox enzymes. In addition, redox polymer 300 is soluble in various common organic solvents, such as alcohol, allowing for easy dissolution and manufacturability.

Redox polymer 300 has, for example, a molecular weight in the range of about 20 Kg/mole to 80 Kg/mole. Furthermore, the mole ratio of p:q can be, for example, in the range of from about 50:1 to about 150:1. The ratio of p:q is predetermined such that the redox polymer has a hydrophilic-hydrophobic balance allowing the hydrophobic polymer backbone, or portion thereof, to be securely attached (e.g., securely absorbed) to an electrode surface. At the same time, the hydrophilic polymer arms of the redox polymer are allowed to freely extend into a liquid sample that immerses such an electrode.

It should be noted that it is the hydrophobic character of MMA that imparts a relatively high degree of hydrophobicity to the hydrophobic polymer backbone of redox polymer 300. Alternative hydrophobic monomers suitable for use in redox polymers according to exemplary embodiments of the present invention include, for example, hydrophobic acrylate or vinyl monomers, such as styrene and butyl methacrylate.

EXAMPLES

Example 1

Synthesis of Compound 1 of FIG. 3

Compound 1 of FIG. 3 was synthesized via free radical co-polymerization using a reaction solution of 10.2 g of NVP, 0.88 g of VFc and 0.05 g of 2,2'-azobisisobutyronitrile (AIBN) in 15 ml of IPEtOH. The synthesis was performed in a round bottom flask.

Before initiating the synthesis, the reaction solution was deoxygenated by bubbling nitrogen therethrough for one hour. The reaction flask was then heated to 70° C. in an oil bath for 24 hours with continuous magnetic agitation under a nitrogen atmosphere. Compound 1 in the reaction solution was dissolved in dichloromethane and precipitated from the reaction solution with diethyl ether. Next, the precipitated Compound 1 was filtrated off and dried in an oven at 50° C.

Example 2

Synthesis of Compound 2 of FIG. 3

Compound 2 was synthesized by reacting 2.0 g of Compound 1 (prepared as described in Example 1 above) with 0.8 g of methacryloylchloride in the presence of 1.2 g of dry triethylamine in 20 mL of dry dichloromethane. The reaction was performed overnight in a round bottom flask at room temperature with continuous magnetic agitation under a nitrogen atmosphere.

The reaction solution was subsequently washed with a solution containing 0.1 N HCl, 0.5 N potassium carbonate and distilled water. The organic phase of the resulting solution was then collected and concentrated by using a rotary evaporator at room temperature under reduced pressure, thereby producing a purified sample of Compound 2. The purified sample of Compound 2 was subsequently dried in an oven at 50° C.

Example 3

Synthesis of a Redox Polymer According to an Embodiment of the Present Invention (i.e., Redox polymer 300 of FIG. 3)

Redox polymer 300 (an ampiphilic polymer) was synthesized by free radical co-polymerization using 1.0 g of Compound 2, 6.2 g of MMA, and 0.06 g of AIBN in 60 mL of 1-pentanol. The reaction was performed in a round bottom flask.

Before initiating the reaction, the 1-pentanol solvent was deoxygenated by bubbling nitrogen therethrough for one hour. The reaction solution was then heated to 70° C. in an oil bath for 24 hours with continuous magnetic agitation under a nitrogen atmosphere. Redox polymer 300 was precipitated out of the reaction solution with diethyl ether and then dried in an oven at 50° C.

Example 4

Electrochemical Evaluation of Redox Polymer 300 of FIG. 3

Figure 4:
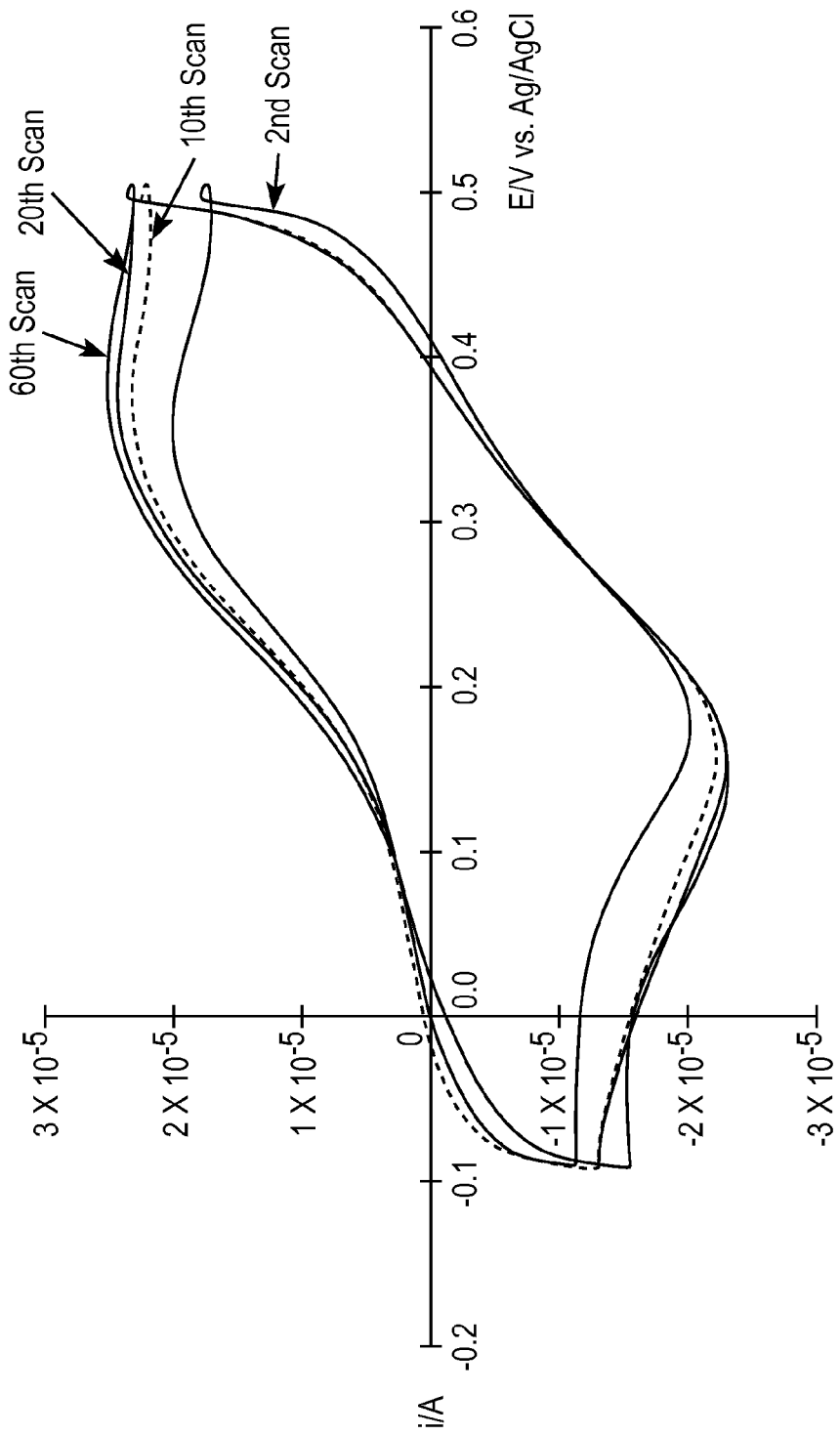
FIG. 4 is a cyclic voltammogram of an electrode coated with redox polymer 300 of FIG. 3.

A glassy carbon electrode (GCE) was dipped into a solution containing redox polymer 300 (prepared as in Example 3 above) dissolved in 2-isopropanol. The GCE was immersed in phosphate buffer saline (PBS) and tested using cyclic voltammetry (CV) at 20 millivolts/second between −0.1 to 0.5 volts vs Ag/AgCl. The presence of reduction and oxidation peaks between the tested voltage range (as shown in FIG. 4) indicated that electroactive ferrocene was immobilized onto the GCE. Sixty CV scans were performed and the results indicated no significant decrease for the oxidation and reduction peaks, which indicates that redox polymer 300 did not wash off the GCE.

Example 5

Electrochemical Evaluation of Compound 2

Figure 5:
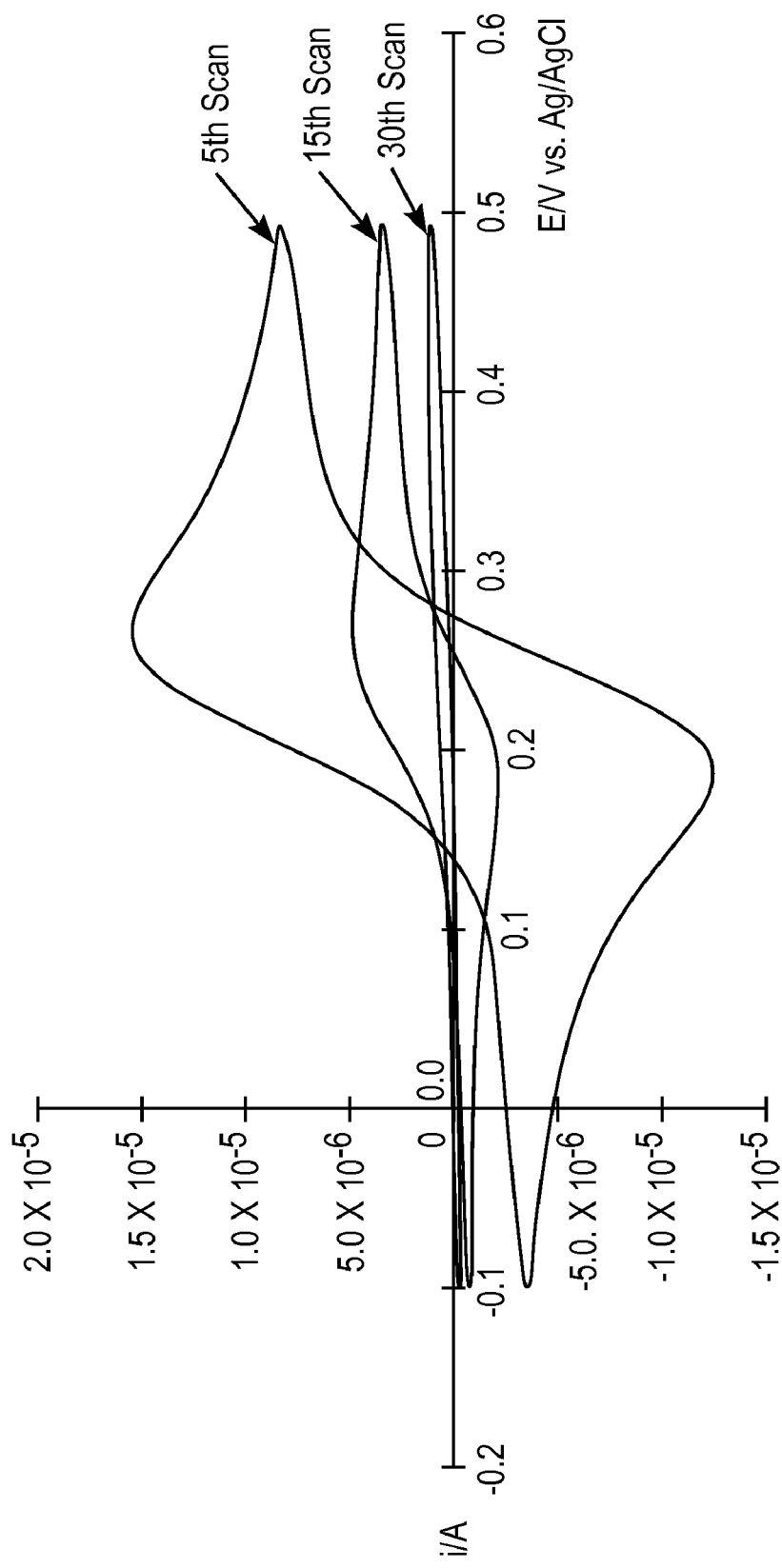
FIG. 5 is a cyclic voltammogram of an electrode coated with Compound 1 of FIG. 3.

A glassy carbon electrode (GCE) was dipped into a solution containing Compound 2 (prepared as in Example 2 above) dissolved in 2-isopropanol. The GCE was immersed in phosphate buffer saline (PBS) and was tested using cyclic voltammetry (CV) at 20 millivolts/second between −0.1 to 0.5 volts. In contrast to Example 4, the magnitude of the oxidation and reduction peaks decreased rapidly upon successive CV scans (as shown in FIG. 5). This indicates that Compound 2 washed off the GCE.

Example 6

Electrochemical Evaluation of Redox Polymer 300 in the Presence of Compound 2

Figure 6:
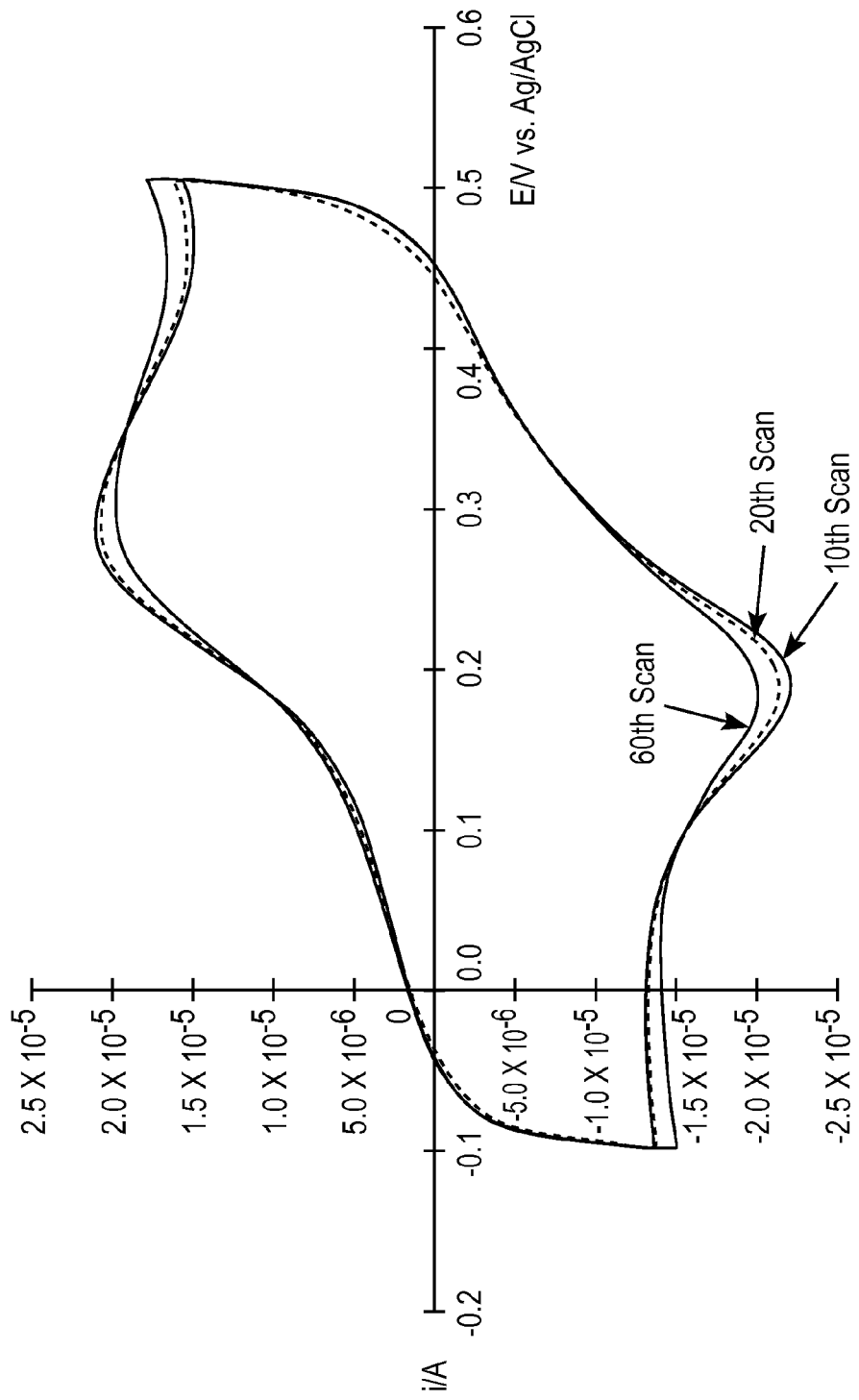
FIG. 6 is a cyclic voltammogram of an electrode coated with a mixture of the redox polymer 300 and Compound 2 of FIG. 3.

A glassy carbon electrode (GCE) was dipped into a solution containing mixture of Compound 2 and redox polymer 300 dissolved in 2-isopropanol. The GCE was immersed in phosphate buffer saline (PBS) and was tested using cyclic voltammetry (CV) at 20 millivolts/second between −0.1 to 0.5 volts. Similar to Example 4, the magnitude of the oxidation and reduction peaks did not decrease significantly after 60 CV scans (as shown in FIG. 6).

This indicates that Compound 2 has a high affinity to the hydrophilic portion of redox polymer 300, causing Compound 2 to also adhere strongly to the GCE. In addition, the separation of the oxidation and reduction peaks in FIG. 6 is smaller than the separation in FIG. 4, which suggests that the mixture of Compound 2 and redox polymer 300 has faster electron transfer kinetics than redox polymer 300 alone and demonstrates a beneficial effect of the homogeneous hydrophilic environment provided by the hydrophilic polymer arms of redox polymer 300.

Figure 7:
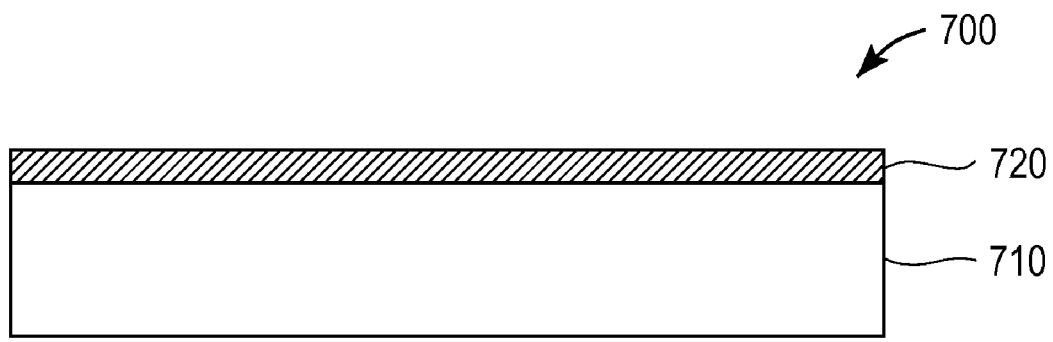
FIG. 7 is a simplified cross-sectional depiction of an electrode of an electrochemical-based sensor according to an exemplary embodiment of the present invention.

FIG. 7 is a simplified cross-sectional depiction of a coated electrode 700 employed in an electrochemical-based sensor according to an exemplary embodiment of the present invention. Coated electrode 700 includes an electrode 710 (such as a carbon electrode) and a chemical composition 720 coated on a surface of electrode 710. The chemical composition includes a redox polymer (as described above) with a hydrophobic polymer backbone, at least one hydrophilic polymer arm attached to the hydrophobic polymer backbone, and a plurality of redox mediators attached to the at least one hydrophilic polymer arm. If desired, the redox composition can also include a redox enzyme, such as, for example, glucose oxidase or glucose dehydrogenase. Such redox enzymes can be, for example, methoxatin-based or nicotinamide adenine dinucleotide based.

It should be understood that various alternatives to the embodiments of the invention described herein may be employed in practicing the invention. It is intended that the following claims define the scope of the invention and structures within the scope of these claims and their equivalents be covered thereby.

What is claimed is:

1. An electrochemical-based sensor comprising:
   an electrode; and
   a chemical composition coated on a surface of the electrode, the chemical composition including a redox polymer with:
      a hydrophobic polymer backbone;
      at least one hydrophilic polymer arm attached to the hydrophobic polymer backbone, the hydrophilic polymer arm formed from at least one of N-vinylpyrrolidone, hydroxyethyl methacrylate, N-isopropylacrylamide, glycerol methacrylate, acrylamide, and combinations thereof; and
      a plurality of redox mediators attached to the at least one hydrophilic polymer arm.

2. An electrochemical-based sensor comprising:
   an electrode; and
   a chemical composition coated on a surface of the electrode, the chemical composition including a redox polymer with:
      a hydrophobic polymer backbone formed from at least one of methylmethacrylate, styrene, butyl methacrylate, and combinations thereof;
      at least one hydrophilic polymer arm attached to the hydrophobic polymer backbone; and
      a plurality of redox mediators attached to the at least one hydrophilic polymer arm.

* * * * *